United States Patent [19]

Comte et al.

[11] Patent Number: 4,714,076
[45] Date of Patent: Dec. 22, 1987

[54] DEVICE FOR THE SETTING OF BONE SEGMENTS

[75] Inventors: Pierre-Andre Comte, Liestal, Switzerland; Caius Burri, Ulm, Fed. Rep. of Germany; Lutz Claes, Ulm, Fed. Rep. of Germany; Heinz Gerngross, Ulm, Fed. Rep. of Germany; Remy Meier, Bubendorf, Switzerland

[73] Assignee: Synthes, Paoli, Pa.

[21] Appl. No.: 680,664

[22] Filed: Dec. 12, 1984

[30] Foreign Application Priority Data

Jan. 19, 1984 [CH] Switzerland .......................... 230/84

[51] Int. Cl.⁴ ............................................... A61F 5/04
[52] U.S. Cl. ............................................... 128/92 ZW
[58] Field of Search .................. 128/92 A, 84, 91 A; 403/90, 56

[56] References Cited

U.S. PATENT DOCUMENTS

| | | | |
|---|---|---|---|
| 2,393,694 | 1/1946 | Kirschner | 128/84 |
| 2,435,850 | 2/1948 | Siebrandt | 128/92 A |
| 4,312,336 | 1/1982 | Danieletto et al. | 128/92 A |
| 4,502,473 | 3/1985 | Harris et al. | 128/92 A |
| 4,541,422 | 9/1985 | Ikowski | 128/92 A |

FOREIGN PATENT DOCUMENTS

| | | |
|---|---|---|
| 2439002 | 10/1978 | France . |
| 608712 | 1/1979 | Switzerland . |
| 633174 | 11/1982 | Switzerland . |
| 2110094 | 6/1984 | United Kingdom . |

*Primary Examiner*—Gene Mancene
*Assistant Examiner*—Wenceslao J. Contreras
*Attorney, Agent, or Firm*—Davis Hoxie Faithfull & Hapgood

[57] ABSTRACT

Bone-setting device comprises two elongated holders which are joined by an elongated connecting link. Pins which can be screwed into bone elements are held in each holder in such a manner that they can be rotated around their axis, moved along that axis, and clamped. At least one holder comprises spherical guiding bodies, each of which holds a pin in such a manner that the pin can be pivoted in space. The connecting link comprises a sleeve and a stud which is held in the sleeve in such a manner that it can be shifted in the axial direction and pivoted, and which, in order to generate a force which presses the bone elements against each other, can, by means of a tensioning screw inserted in it, be pulled against one end of sleeve and clamped in various pivoting and sliding positions by means of a clamping screw. The device offers many adjusting possibilities for setting the bone elements but is, nevertheless, very rigid in the clamped state and also relatively small and easy to handle.

30 Claims, 11 Drawing Figures

DEVICE FOR THE SETTING OF BONE SEGMENTS

The invention relates to a bone-setting device and in particular to a device useful for setting bones, such as arm or leg bones, after a fracture or osteotomy by means of pins inserted into the bone segments through the skin from outside the body.

In the treatment of a bone fracture the bone segments are usually set with a bone-setting device. In some cases resetting by adjusting parts of the device may be necessary. Sometimes the bone segments can be provisionally set with the bone-setting device at the place of the accident and then permanently set in the hospital.

A bone-setting device described in Swiss Pat. No. 608,712 comprises nails which pass through the bone being set and whose ends are fastened to struts located on the opposite sides of the bone. Each strut is formed by two rods connected by a joint. Each joint comprises two components in each of which one of the rods is held in such a manner that it can be rotated around its longitudinal axis and can be clamped in various rotational positions. The two joint components in turn are rotatable around a pin connecting them and can be clamped in various different rotational positions. Clamping devices with one part which can be clamped to the struts and another part which can be rotated in relation to the first part and which clamps the nails in a displacable manner are provided for fastening the nails to the struts.

In this bone-setting device of Swiss Pat. No. 608,712, it is necessary to provide a strut on each side of the bone, which represents a considerable inconvenience for the patient. Moreover, in spite of the large number of adjustable parts it is practically impossible, with this device, to rotate the bone fragments around their longitudinal axis in relation to each other in order to adjust their relative position. This is particularly disadvantageous in cases where the bone segments are to be provisionally set at the place of the accident to avoid soft tissue damage during transportation because in these cases it is usually impossible to position the bone segments at the place of the accident in such a manner that they can afterwards be put into the correct position by adjustment of the components of the bone-setting device. It is also desirable in many instances to reset the bone segments after they have been provisionally set and to press them against each other at the of the fracture, a procedure which is not possible with the above bone-setting device; or is at best possible only by the use of an additional tensioning device. It has also been observed in practice that the device was frequently not rigid enough, so that it was, if possible, used without joints.

Another bone-setting device, described in U.S. Pat. No. 4,312,336, comprises two holders in which pins that are to be screwed into the bone segments are clamped. The pins are movable along their axis. A connecting link is provided which comprises a sleeve and a stud which is positioned in the sleeve and can be clamped in various axial positions. The sleeve and the stud are each connected to one of the two holders by a ball joint. Each ball joint comprises a multi-part body which supports a ball. In order to permit clamping of the ball, the joint body comprises a threaded ring which can be tightened, and two clamping screws. A tensioning device is provided for generating axial tension, said device comprising a threaded sleeve and a supporting sleeve for supporting a tensioning screw which engages the threaded sleeve. Each of the two sleeves comprises a fastening bolt which is positioned transversally to its axis and can be inserted in transverse holes in the sleeve and the stud of the connecting link.

In this device the two holders can be rotated in relation to each other around the longitudinal axis of the connecting element. However, the pins held by the same holder must, of necessity, all be parallel to one another, which greatly reduces the possibilities for setting the bone segments. As the holders, each of which holds several pins, form comparatively long lever arms in relation to the ball joints, they can, when the device is in use, exert comparatively large torques on the ball joints so that, in spite of the elaborate design of these ball joints and of the means used to clamp the, there is the danger that the ball joints will move when a force is exerted on them, even if they are clamped tight. The handling and use of the device are also made more difficult by the fact that the tensioning device is not permanently integrated with the device, but first has to be attached to its connecting link and then positioned along the latter. The manufacture of the device is also very expensive.

Another bone-setting device of possible interest is that disclosed in Swiss Pat. No. 633,174. This device however, is designed exclusively for the positioning of vertebrae.

It is an object of the present invention to provide a bone setting device for the external fixation of bones which will permit the desired rigidity also while permitting the necessary adjustability of the bone segments held in position by the device.

This and other objects are met, in accordance with the invention, by means of a bone-setting device having a plurality of pins for insertion into the bone fragments, a pair of holders for holding said pins while permitting longitudinal movement thereof, a connecting link, hinges joining said connecting link to each of said holders, said hinges permitting rotation of each of said holders about an axis perpendicular to the longitudinal axis of the holders and of the connecting link and means for clamping said holders at various positions about said axis.

The invention will be further described with reference to the accompanying drawings in which.

Figure 1:
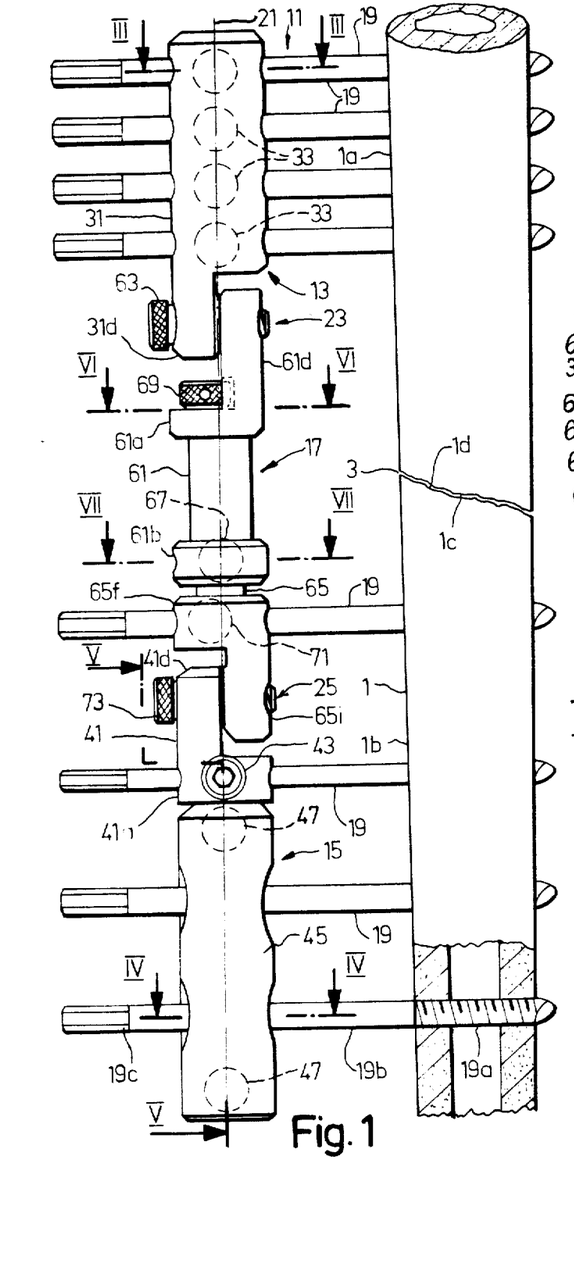
FIG. 1 is a view in side elevation of a bone and a bone-setting device, according to the invention.

Referring to the drawings, FIG. 1 shows a part of a human bone 1, e.g. the long bone of a leg or possibly an arm, which is broken at fracture point 3 into two pieces or fragments, 1a, 1b, with the fracture surface of the two pieces or fragments of the bone being designated by 1c and 1d, respectively. The bone segments 1a, 1b are positioned in relation to each other by means of the external bone-setting device 11. The device comprises two holders 13 and 15 which are joined by connecting link 17 located between them. Also provided are pins 19, so-called Schanz screws, which are screwed into the bone and each of which comprises a threaded part 19a, a cylindrical shank 19b and a hexagonal end 19c which can be gripped with a wrench. The two holders 13, 15 and connecting link 17 are located outside the patient's body and the shanks of the pins 19 enter the patient's bone through his skin, which is not shown. In the device shown, holder 13 can carry four pins, connecting link 17, one pin and holder 15, three pins. The pins are retained in transverse holes or channels in the holders 13, 15 and link 17 in such a manner that all pins can be loosened. Connecting link 17 is attached by a hinge 23 to holder 13 and by a hinge 25 to holder 15.

The two holders 13, 15 and the connecting link 17 are elongated and can be clamped in relation to each other in positions in which they are aligned along a common longitudinal axis 21. The holders and the connecting link have, disregarding protruding screws, approximately the shape of a circular cylinder, are coaxial with longitudinal axis 21, and have approximately the same diameter.

Figure 2:
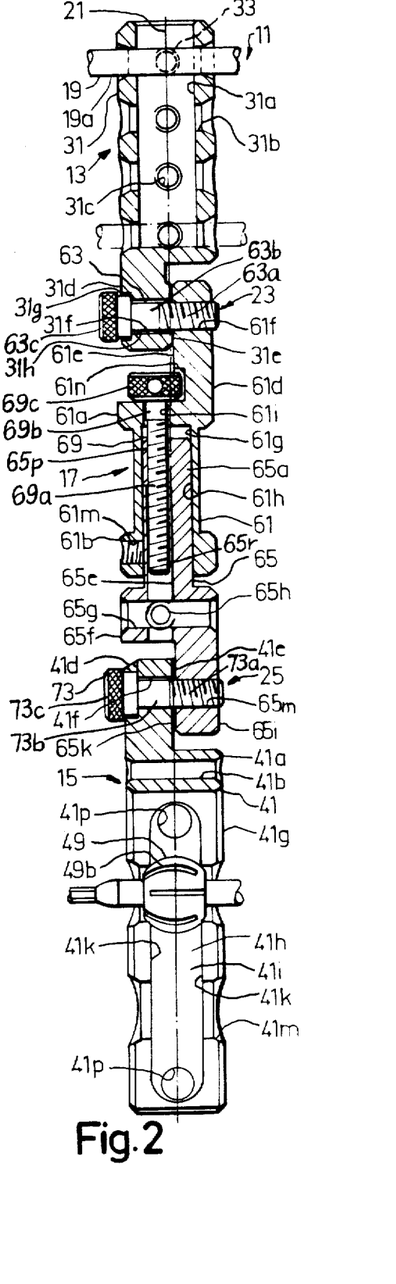
FIG. 2 is a view in vertical section through the device shown in FIG. 1, with a few of the insertable pins omitted.
Figures 3, 4, 5:
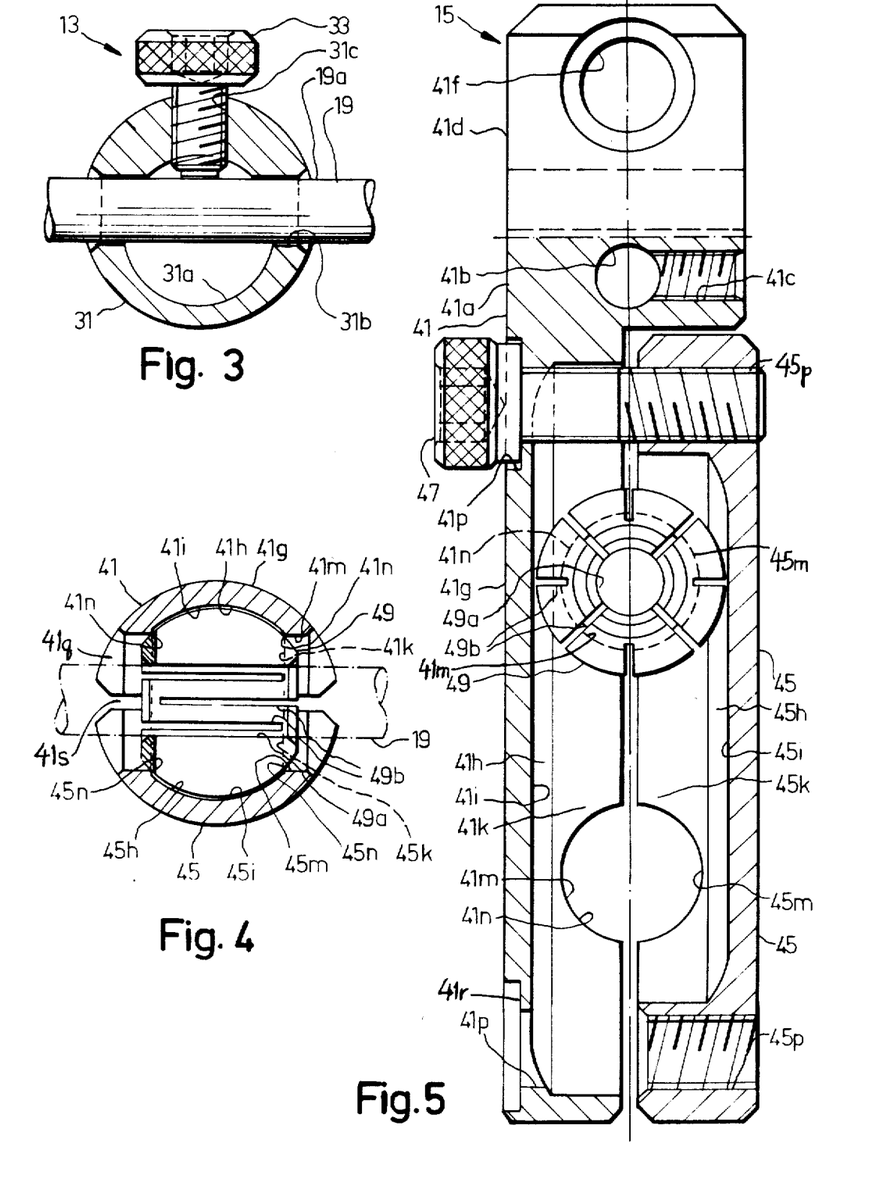
FIG. 3 is an enlarged view in horizontal section along line III—III of FIG. 1.
FIG. 4 is an enlarged view in horizontal section along line IV—IV of FIG. 1.
FIG. 5 is an enlarged view in vertical section along line V—V of FIG. 1, with several parts omitted.

The design of holder 13 is shown in FIGS. 1, 2 and 3. The main part of the holder consists of body 31 which generally has the shape of a circular cylinder and is made in one piece. Body 31 comprises a blind longitudinal hole 31a which is parallel to but eccentric to its center line, and opens onto the end of body 31 which lies opposite connecting link 17; the purpose of this hole is to save weight. Body 31 comprises, for each pin 19 which it carries, a transverse through hole 31b which intersects its longitudinal axis and the longitudinal hole 31a at a right angle. A hole such as hole 31b accommodates shank 19b of pin 19 with small radial play, permitting rotation about the pin's longitudinal axis and longitudinal translation along this axis. A conical countersink is preferably provided at each of the two ends of each transverse hole 31b. On the side of the center line of body 31 opposite the axis of the eccentric longitudinal hole 31a there is provided for each pin 19 a tapped hole 31c (FIG. 5) perpendicular to the center line of said body. The holes 31c accommodate clamping screws such as screw 33 for clamping pins 19 to body 31. The screws 33 comprise a threaded part engaging the tapped hole 31c, and a head.

At the end facing connecting link 17 the body 31 comprises an extension 31d which has an approximately semicircular cross section and can be formed by cutting approximately one-half of a cylinder out of the end part of body 31 along the axis of said body. As will be explained below, extension 31d serves as a part of hinge 23 and comprises a flat contact surface 31e, which extends along and preferably through the centerline of body 31 and is perpendicular to the axis of the transverse holes 31b. A through hole 31f is provided perpendicular to said contact surface 31e and thus parallel to the axis of the through holes 31b and of the pins 19. This hole 31f consists of a shouldered larger section 31g and a smaller-diameter part 31h. The smaller part opens onto the contact surface 31e and a larger part opens onto the surface of extension 31d which surface has an approximately semicircular profile.

Referring to FIGS. 1, 2, 4 and 5 the other holder 15 comprises a body 41 with a short cylindrical section 41a containing a through hole 41b transverse to its axis. In said hole may be inserted one of the pins 19 in such a manner that it can be rotated and longitudinally displaced; and can be clamped by means of a clamping screw 43, which is screwed into a tapped hole 41c. On the side of section 41a which faces connecting link 17 there is an extension 41d which is similar to extension 31d and has a flat contact surface 41e and a transverse hole 41f. Contact surface 41e is parallel to the longitudinal axis of holder 15 and in particular to that of the cylindrical section 41a and lies preferably directly in this longitudinal axis and perpendicular to the axis of transverse hole 41f. The cylindrical section 41a also comprises a clamping element 41g whose cross section is a curved segment extending not quite over one-half of the circumference of a circle. The chord drawn across the semi-circular outline of the cross section of clamping element 41g is perpendicular to contact surface 41e. On the side bounded by said chord and facing the longitudinal axis of holder 15, clamping part 41g defines an oblong recess 41h. This recess is bounded by the internal concavely curved surface 41i of clamping element 41g and by two flat side surfaces such as 41k which are parallel to each other. The side walls which form said side surfaces 41k and form the boundaries of recess 41h on its two opposing longitudinal sides are intersected by two grooves 41m which are located at a distance from each other along the longitudinal axis of clamping element 41g. They intersect recess 41h perpendicularly and their cross-sections form, as shown in FIG. 5, circular arcs of somewhat less than 180°. The middle, inner part of each groove 41m to the extent it does not fall in the area of recess 41h, is bounded by a surface forming a cylindrical segment. Where this surface intersects the two side surfaces 41k, edges 41n are formed which conform to circular arcs. As will be explained below, these edges 41n serve as clamping devices. At their ends which open onto the outer surface, which forms a cylindrical segment of clamping element 41g, the grooves 41m are bounded by oblique conical surfaces 41g which become wider toward the outside. Clamping element 41g furthermore comprises two through holes 41p, which have shoulder 41r at one end.

Holder 15 further comprises a second separate clamping element 45. The latter is formed by an oblong rod-shaped body whose cross-section has the general shape of a circular segment not quite a semicircular. Clamping element 45 is slightly shorter than clamping element 41g. The curved sides of the two clamping elements 41g, 45 face each other and their cross-sections are at least substantially symmetrical to each other in respect to the plane located between them. Clamping element 45 comprises recess 45h which is bounded by a curved bottom surface 45i and flat side surfaces 45k and is somewhat shorter than recess 41h but is symmetrical with the latter. Clamping element 45 furthermore comprises grooves 45m which are located symmetrically to the grooves 41m. At the intersection between the grooves 45m and the side surfaces 45k, circular, arc-shaped edges 41n are formed which function as clamping devices 45n symmetrical to the edges 41n. Clamping element 45 comprises two tapped holes 45p which are located in the end sections of clamping element 45 which form the boundaries of recess 45h at its ends and are each in line with the through holes 41p of clamping element 41g. Clamping element 45 is fastened to clamping element 41g by two clamping screws 47 which are screwed into the tapped holes 45p through the holes 41p. Only one screw 47 is shown in FIG. 5.

Two guiding bodies 49 which are ball-shaped, or more exactly have spherically shaped outer surfaces, are located between the two clamping elements 41g and 45 in the area of their grooves 41m and 45m, respectively, which are paired off, facing each other. Only one guiding body 49 is shown in FIGS. 2 and 5. The guiding bodies 49 have a through hole 49a passing through their center which is formed with a conical countersink at each end. The shank 19b of one of the pins 19 is rotatably supported in hole 49a with small radial play and held so that it is displacable in its longitudinal direction. Each guiding body 49 comprises several, for example eight, grooves 49b which are distributed over its periphery, are parallel to the axis of through hole 49a and extend radially from the circumferential surface of guiding body 49 into through hole 49a. The grooves 49b are somewhat shorter than through hole 49a and start along the circumference alternately at opposite ends of the through hole. The guiding body 49 is therefore divided by the grooves 49b into segments which are alternately elastically joined on opposite ends by webs.

The diameter of the guiding bodies 49 is chosen in such a way that the two clamping elements 41g and 45, when their clamping edges 41n and 45n are in contact with the guiding bodies 49, are separated from each other by a slot 41s on the side. The centers of the guiding bodies are located at this slot, on the longitudinal axis of holder 15 which, in the position shown in FIGS. 1 and 2, coincides with longitudinal axis 21. When the two clamping screws 47 are loosened, the two pins 19, each of which passes through one of the guiding bodies 49, can be rotated around their longitudinal axes, shifted in their longitudinal direction and, in addition, pivoted in space together with the guiding bodies 49, around the centers of the latter. Based on the mid-positions of the pins 19 and guiding bodies 49 shown in FIGS. 1, 2, 4 and 5, the maximum pivoting angle is at least 20° and approximately 25° in all directions. If the two clamping screws 47 are tightened, the two guiding bodies 49 are compressed between the clamping elements 41g, 45 and clamped, and in turn clamp the pins 19 which are located in them. As the clamping elements 41g, 45 grasp the guiding bodies 49 on the arc-shaped clamping edges 41n and 45n, or, at the most, by very narrow strips of surface located along these edges, relatively high pressures are generated when the clamps are tightened, which ensures reliable clamping of the guiding bodies in the chosen pivoting position.

The design of the parts of the bone-setting device 11 which form the connecting link 17 and the hinges 23, 25 is shown in FIGS. 1, 2, 5, 6, 7, 8 and 9. Connecting link 17 comprises a sleeve 61 with a cylindrical main part whose longitudinal axis coincides in the position shown in FIGS. 1 and 2 with longitudinal axis 21 and carries at both ends flange-like collars 61a and 61b, respectively, whose outside diameter is at least approximately the same as the outside diameter of body 31 of holder 13 and that of the cylindrical part 41a of holder 15. Attached to collar 61a, which is nearer to holder 13, is an extension 61d which is eccentric to the axis of the sleeve, whose outside surface is in line with a segment of the periphery of the collar 61a and whose free end section forms on its side facing the axis of the sleeve a flat contact surface 61e. A tapped hole 61f is provided through extension 61d perpendicular to contact surface 61e. Extension 31d of holder 13 and extension 61d each form one element of hinge 23, with the two extensions making contact with each other by means of their surfaces 31e, 61e which face each other. A hinge bolt 63 comprises a threaded part 63a which is screwed into the tapped hole 61f, a bearing part 63b which passes through the through hole 31f and pivotably supports holder 13, and a head 63c. If hinge bolt 63 is loosened, holder 13 can be pivoted in relation to connecting link 17 around the axis of bolt 63, which is parallel to the axes of the through holes 31b. If, however, hinge bolt 63 is tightened, the shoulder surface which is located at the transition between its bearing part and its head and is formed by a radial surface of the latter presses extension 31d against extension 61d and thereby clamps these parts in the chosen position.

Figures 6, 7, 8, 9:
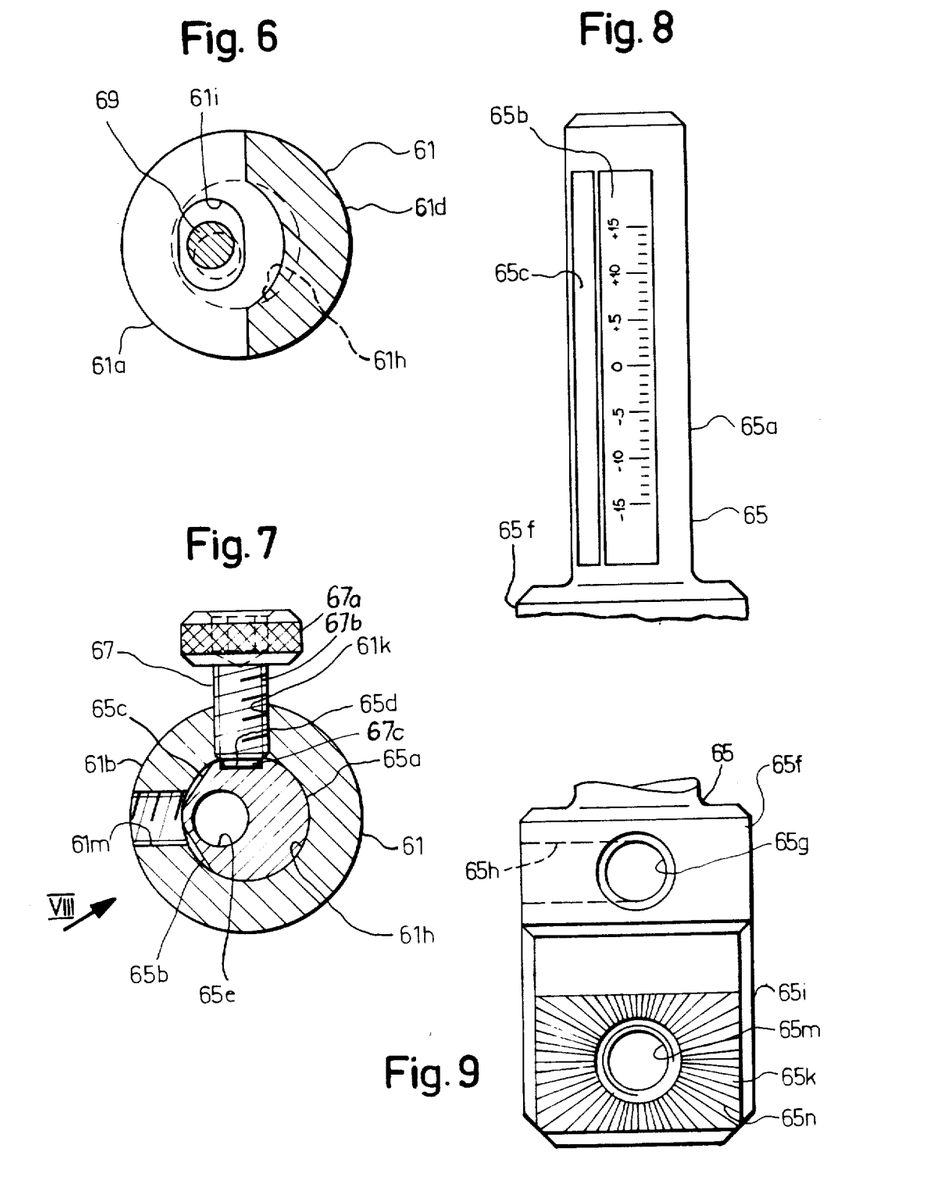
FIG. 6 is an enlarged view in horizontal section along line VI—VI of FIG. 1.
FIG. 7 is an enlarged view in horizontal section along line VII—VII of FIG. 1.
FIG. 8 a view of part of the stud in the direction of view indicated by arrow VIII in FIG. 7.
FIG. 9 a top view of the contact area formed by the extension of the stud.

Sleeve 61 comprises longitudinal hole 61g which extends through its entire length and has a main part 61h. The hole 61g is cylindrical and coaxial with the axis of the sleeve 61, and opens onto the end surface of a collar 61g facing toward holder 15. Longitudinal hole 61d has an end portion 61i which faces holder 13, and which is eccentric to the axis of the sleeve, i.e., shifted to the side opposite extension 61d. FIG. 6 shows that the cross section of end portion 61i has the shape of an elongated slot whose major dimension is parallel to the chord formed in cross section by extension 61d. End portion 61i, in an axial projection, lies completely within the cylindrical part 61h of the longitudinal hole 61g and thus forms an eccentric narrowing of the latter. Within the area of collar 61b which faces toward holder 15, the sleeve 61 comprises two tapped holes 61k and 61m, shown in FIG. 7, and as to 61m, also in FIG. 2. The two tapped holes 61k, 61m are both perpendicular to the axis of the sleeve, and open into the cylindrical part 61h of longitudinal hole 61g. They are displaced in relation to each other along the periphery of the sleeve by an arc or angle of, for example, 90°, with their axes lying in the same plane as shown in FIG. 7, perpendicular to the axis of the sleeve.

Stud 65 which is shown particularly clearly in FIGS. 2, 7, 8 and 9, comprises a part 65a with a periphery, part of which has the shape of a circular cylinder. Said part 65a is supported rotatably or pivotably and with little radial play in the cylindrical part 61h of the longitudinal hole 61g of the sleeve and is axially movable therein. The periphery of stud part 65a comprises three flats or recesses forming clamping surfaces 65b, 65c, 65d which are positioned over the stud periphery and are somewhat shorter than stud part 65a (FIG. 8). The two clamping surfaces 65b and 65c are flat and in the cross section shown in FIG. 7, are chords of stud part 65a, while clamping surface 65d is formed by the flat bottom of a groove, whose side longitudinal surfaces are perpendicular to clamping surface 65d. The three clamping surfaces 65b, 65c, 65d are, for example, distributed over approximately one-half the periphery of stud part 65a, and the pairs of successive clamping surfaces form angles, e.g. 120° angles, with each other, with a narrow strip of the cylindrical periphery being preserved between successive clamping surfaces. Clamping screw 67 comprises a head 67a and a threaded part 67b which carries at its end opposite the head a thinner cylindrical extension 67c. Screw 67 can be screwed into one or the other of the tapped holes 61k and 61m. In FIG. 7, clamping screw 67 is inserted into tapped hole 61k and its extension protrudes, with very little lateral play, into the groove whose bottom forms clamping surface 65d, so that, if clamping screw 67 is screwed in loosely, the extension 67c guides stud 65 while it is moved longitudinally and secures it against twisting. If, on the other hand, the clamping screw is tightened, the flat front end of its extension makes contact with clamping surface 65d of the stud and clamps it tightly in the position shown in the drawing -- against pivoting and longitudinal movement. This position with regard to pivoting will hereinafter be called mid-position with regard to pivoting. If clamping screw 67 is removed from tapped hole 61k, the stud can be pivoted by 30° from mid-position in one or the other direction as desired, clamping screw 67 can be inserted into tapped hole 61m and used to clamp the stud, depending on its pivoting position, against clamping surface 65b or 65c. The stud can therefore be clamped in any of three different pivoting positions and in continuously adjustable sliding positions. Stud 65 may have on its clamping surface 65b, a scale extending in its longitudinal direction; the scale indicia coinciding with the front surface of collar 61b then indicates the longitudinal position of the stud. The scale, starting from the zero mark, may comprise dimensional markings, for example, in millimeters.

As shown in FIG. 2, stud 65 also comprises a longitudinal hole 65e which is parallel to but eccentric to its longitudinal axis. It can be a through hole which opens onto the end surface of stud part 65a, or possibly a blind hole. At least part of this longitudinal hole 65e, advantageously at least its end part 65p facing holder 13, comprises an internal thread, while the remaining part 65r has a diameter which is somewhat larger than the thread diameter. A tensioning screw 69 is provided, comprising a threaded part 69a, which engages the internal thread of longitudinal hole 65e, a shank 69b passing through the eccentric end part 61i of longitudinal hole 61g of sleeve 61, and a head 69c. The slot-shaped design of end part 61i of the longitudinal hole 61g, through which the shank 69b of tensioning screw 69 passes, and the play of the shank of the screw in said end part ensure that said 65 may be rotated into its alternative positions described above in spite of the eccentric location of screw 69 in stud 65. The head 69c of tensioning screw 69 is located between the front surface of collar 61a and the contact surface 61e of extension 61d and partly extends into a recess 61n provided in said extension. If tension screw 69 is screwed deeper into stud 65, the radial shoulder surface formed by its head makes contact with the surface of collar 61a which faces holder 13 and is perpendicular to the axis of sleeve 61. If clamping screw 67 is loosened, stud 65 can be pulled deeper into sleeve 61 by screwing tensioning screw 69 into said stud. This action generates a force which is parallel to the longitudinal axis of connecting link 17, pulls the two holders 13, 15 toward each other, and presses the fracture surfaces 1c, 1d against each other.

At the end of stud segment part 65a which protrudes from sleeve 61, there is attached a cylindrical wider part 65f whose diameter is at least approximately equal to those of body 31 and collars 61a, 61b. The part 65f has a transverse hole 65g in which one of the pins 19 is supported rotatably and movable longitudinally. A clamping screw 71, which can be used to firmly clamp the pin 19 in question, is screwed into the tapped hole 65h which is transverse to through hole 65g and opens into said hole. The end of stud 65 facing holder 15 constitutes an extension 65i, comprising contact surface 65k which makes contact with contact surface 41e of extension 41d of holder 15. Extension 65i is provided with a tapped hole 65m. If stud 65 is in the illustrated pivoting mid-position in relation to sleeve 61, the flat contact surface 65k is parallel to the flat contact surface 61e and lies in the same plane as the latter. Hinge bolt 73, designed similarly to hinge bolt 63 comprises a threaded part 73a screwed into the tapped holes 65m and a bearing part 73b which passes through through hole 41f and supports holder 15 in such a manner that it can be pivoted in relation to connecting link 17. Hinge bolt 73 also has a head 73c by means of which the extensions 41d and 65i which form the hinge parts of hinge 25 can be pressed against each other and firmly clamped.

The contact surfaces 31e, 61e and 41e, 65k which are in contact with each other by pairs, each comprise a serrated crown of alternately successive teeth and grooves which extend along straight lines radiating from the pivoting axes defined by the hinge bolts 63, 73. These teeth and grooves form meshing surfaces, of which that of contact surface 65k is shown in FIG. 9 and indicated by the reference numeral 65n. If the contact surfaces 31e, 61e and 41e, 65k are pressed against each other by tightening of the hinge bolts, these meshing surfaces engage each other, so that the hinges 23, 25 cannot, if they are clamped together, move in relation to each other even if very large forces and torques are applied. The pitch of the meshing surfaces is comparatively fine and each surface may comprise, for example, approximately 120 teeth, so that the hinges 23, 24, in spite of the meshing surfaces, can be held in fixed pivoting positions which are practically continuously variable.

The heads of the various clamping screws 33, 43, 47, 67 and hinge bolts 63, 73 advantageously comprise peripheral surfaces which at least over part of their length are provided with a knurl or similar pattern. The heads of the clamping screws and hinge bolts also comprise on their faces a hexagonal hole for receiving an Allen wrench. The head of tightening screw 69 carries is also knurled over at least part of its length and comprises at least one hole, that is accessible from the side, for example, a hole extending diametrically through the head, for the insertion of a wrench with a suitable pin.

All the parts of the bone-setting device which are described above may consist of metal, for example stainless steel or titanium alloy.

Before it is applied, the bone-setting device is advantageously in a condition in which the two holders 13, 15 and the connecting link 17 are aligned along the common longitudinal axis 21. Stud 65 is in the pivoting mid-position, as shown in the drawing, and the longitudinal axes of all through holes 31b, 41b, 49a, 65g which are used to guide pins 19 are lying in the same plane and are parallel to each other. Stud 65 is in the mid-position relative to sliding in sleeve 61, a position in which the zero marking of the scale applied to clamping surface 65b coincides with the front face of collar 61b. If the device 11 is now to be used for setting a bone, the bone segment 1a can, for example, by first provisionally set by means of two pins 19 inserted in holder 13, and bone segment 1b can be provisionally set by means of two pins 19 inserted in the guiding bodies 49 of holder 15. In case of a bone fracture caused by an accident, this can be done at the location of the accident. If subsequent resetting of the bones makes it necessary to rotate the pins 19 held by holder 15 in relation to the pins held by holder 13 and to perform this rotation around the longitudinal axis 21, the clamping screws 47 can be temporarily loosened and the guiding bodies 49 can be rotated as required. If this is not sufficient, stud 65 can be pivoted from its mid-position in relation to sleeve 61 and clamped in one of the other pivoting positions provided. It is also, of course, possible to rotate holder 13 in relation to sleeve 61 with hinge bolt 63 as the center of rotation, and holder 15 in relation to stud 65 with the hinge bolt 73 as the center of rotation and to clamp them in various pivoting positions. After the bone fragments 1a, 1b have been set, it is possible, by means of tensioning screw 69, and with the clamping screw 67 temporarily loosened, to generate a force which presses fracture surfaces 1c and 1d against each other.

It is also possible to insert, if necessary during the adjustment process, more than four pins. For example, if the bone has been fractured into three pieces, the bone segment in the middle can be set by means of at least one pin which can be clamped in the transverse hole 65g in part 65f or in part 41a of body 41. In this connection it should be noted that the locations of the two holders 13 and 15 can be reversed.

It is also possible to keep a set of holders 13, 15, connecting links 17 and other components in readiness, so that the surgeon, if necessary, can attach to both ends of a connecting link 17 a holder like holder 15 which can hold pins 19 in such a manner that they can be rotated in space. On the other hand, if the surgeon has such a set of components available he can, in simple cases, assemble a bone-setting device which comprises at each end of connecting link 17 a holder which is designed in the same manner as holder 13 and which does not carry any pins which can be rotated in space.

It should be mentioned furthermore that the device can be used not only for the setting of bone segments created by a bone fracture, but also for the setting of bone segments which were generated by osteotomy, i.e. the surgical severing of bone. After an osteotomy it is frequently necessary to distract, i.e. stretch, the bone and to apply forces in opposite directions to the bone segments after they have grown more or less together. Such a stretching of the bone can also be achieved with the bone-setting device 11, by unscrewing tensioning screw 69 during the therapeutic and healing process in small steps, i.e. by screwing it out a predetermined distance from stud 65 with clamping screw 67 being loosened temporarily. The head of tensioning screw 69 then engages the surface of recess 61n which is opposite collar 61a. This pulls stud 65 a certain distance out of sleeve 61 and increases the distance between the two hinges 23, 25 and, of course, also between the two holders 13, 15. This can take place for all possible pivoting positions of holder 13, which is articulated to extension 61d.

The bone-setting device thus makes it possible to set the bone segments created by a fracture or osteotomy and to do so with many degrees of freedom. After the adjustable parts of the device have been clamped firmly, it is very rigid, in spite of the many adjustment possibilities. In this respect it is an advantage that each of the guiding bodies 49, which are rotatable in space, transmits only the force of a single pin and is relatively close to the point where the bone exerts a force on that pin.

The device is also relatively small and easy to handle. Compared to the bone-setting device of Swiss Pat. 608,712 referred to above and in which the pins passing through the bone have to be clamped in holders on both sides of the bone, bone-setting device 11 of the invention has the great advantage for the comfort of the patient that the pins have to be clamped on only one side of the bone by means which are outside of the body. The device 11 of the invention can also be disassembled and cleaned in a comparatively short time, which is an advantage because the device has been developed for repeated use, with the exception of the pins.

The device can, of course, be modified in various respects. For example, the holes 41b, 65g which are used for guiding pins 19 can be omitted. The number of pins carried by holder 13 and the number of pins carried by holder 15 in such a manner that they can be rotated in space and moved longitudinally, may vary. Holder 13 should, however, carry at least one pin and preferably at least two pins and holder 15 should carry at least one pin and preferably at least two pins in such a manner that they can be rotated in space and moved longitudinally. Apart from the abovementioned possibility of holding a set of components in readiness which enable the surgeon to select a suitable holder, it is also possible to keep a complete device in readiness, in which, for example, holder 13 is replaced by a holder which is designed to hold at least one pin in such a way that it can be rotated in space.

Part 65a of stud 65, instead of the three clamping surfaces 65b, 65c, 65d, can comprise other clamping surfaces which are not rotationally symmetrical in relation to the axis of the stud, i.e. which in cross section do not form convex circular arcs around on the axis of the stud. Instead of the three flat clamping surfaces 65b, 65c, 65d shown in the drawing, concave clamping surfaces can be provided. Furthermore the number of clamping surfaces can be larger or smaller than three. For example, only one clamping surface can be provided, and sleeve 61 can comprise three or more tapped holes distributed along its periphery, into one of which, as required, a clamping screw for clamping the stud in position can be inserted. If at least two clamping surfaces of the type referred to are provided, the sleeve will, of course, have to comprise only one single tapped hole with a clamping screw serving to clamp the stud in position.

The end section 61i of the longitudinal hole 61g which passes through collar 61a, instead of being formed by a straight slot, can consist of a slot which curves around the axis of the sleeve.

The ball-shaped guiding bodies, instead of notches, can have comprise only slots whose two ends are bounded by webs of the guiding body.

Figure 10:
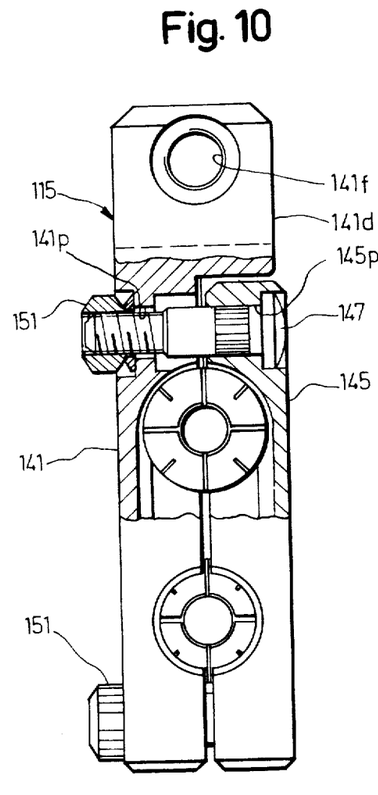
FIG. 10 a modified version of the holder for clamping ball-shaped guiding bodies.

The holder 115 shown in FIG. 10 comprises a body 141 and a clamping element 145 and corresponds in general to the holder 15 whereby reference numerals of correspondind members have been increased by 100. The tapped holes 45p of the clamping element 45 are replaced by unthreaded holes 145p having a wider counter- bore at the end opposite to the body 141. Each screw 47 is replaced by a bolt 147 having a threaded end portion, a thickner, threadless shaft portion and a head. The shaft portion of this bolt 147 is pressed firmly in the hole 145p so that the head of the bolt is arranged in the counter bore. The threaded portion of the bolt penetrates the hole 141p and is fixed with a nut 151 comprising a slightly springy washer hold rotatably and unseparably on the nut.

Figure 11:
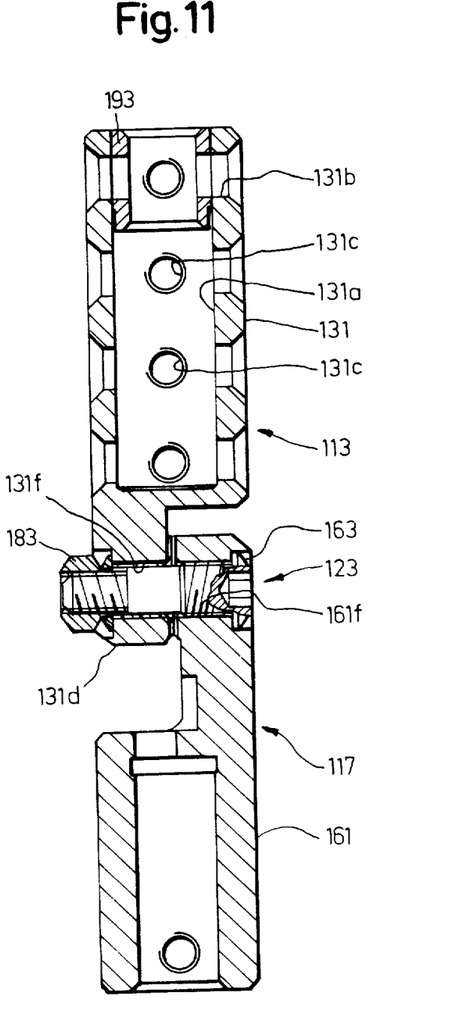
FIG. 11 a modified version of a hinge and the other holder.

The two hinges 23, 25 can also be modified. FIG. 11 shows for instance a holder 113 connected by a hinge 123 with a connecting link 117 whereby parts generally corresponding to parts of the bone setting device 11 are designated by reference numerals increased by 100. The tapped hole 161$f$ of the sleeve 161 and the not shown hole corresponding to the hole 65$m$ of the stud 65 can for instance be provided at their ends facing away from the extensions 131$d$ and 141$d$ (FIG. 10), respectively, with a wider counter-bore. The hole 31$f$ of the body 31 is replaced by a tapped hole 131$f$ having the same diameter as the tapped hole 161$f$ and the hole 141$f$ (FIG. 10) is modified accordingly. The hinge bolt 63 is replaced by a hinge bolt 163 having, lined up along its axis, a head, a first threaded portion adjacent to the head, a thinner, cylindrical bearing portion and a still thinner second threaded portion forming the bolt end opposite the head. The first threaded portion has the same nominal diameter as the mentioned tapped holes 131$f$, 161$f$ and is screwed into the tapped hole 161$f$ so that the bolt head engages the radial surface of the said counter-bore. The cylindrical bearing portion of the hinge bolt penetrates the tapped hole 131$f$ and has a diameter that is approximately equal to the minimum diameter of the tapped hole 131$f$ or slightly smaller than this diameter so that it can rotatably journal the body 131. The second threaded portion of the hinge bolt 163 protrudes out of the tapped hole 131$f$. On the second threaded portion is screwed a nut 183 with a slightly springy washer mounted to the nut so that the washer can rotate in relation to the nut but not be separated from the latter. The hinge bolt 73 of the device 11 is replaced by a hinge bolt not shown in FIG. 11, formed in the same way as the bolt 163 and mounted in an analogous manner as the bolt 163. By screwing on the nuts more or less strongly one can either clamp the holders rigidly to the connecting link or achieve a rotatable connection of the holders with the connecting link. Of course it would also be possible to screw the first threaded portions of the hinge bolts into the tapped holes of the holders so that the bearing portions would then penetrate the tapped holes of the connecting link. The two threaded portions of the hinge bolt may be threaded in the same sense or in opposite senses. The first threaded portion of the hinge bolts and the tapped holes of the coupling link and the holders can for instance have left-handed threads and the second threaded portions of the hinge bolts and the nuts can have right-handed threads.

Thus the modification of the hinges described in the preceeding paragraph allows to connect two holders separably with a connecting link in a similar manner as it is shown in FIG. 1 for the holders 13, 15 and the connecting link 17. The execution of the hinges described in the preceeding paragraph allows in addition to omit the connecting link and to connect directely two holders by one of the described hinge bolts. The first threaded portions of the hinge bolt can for this purpose be screwed into the tapped hole of one of the two holders and the bearing portion of the hinge bolt penetrates then the tapped hole of the other holder. A nut of the described kind can be screwed on the second threaded portion of the hinge bolt protruding out of the tapped hole of said other holder. The same two holders can, therefore, be connected either by means of the connecting link and two hinge bolts or directly with one hinge bolt without connecting link whereby the same hinge bolts and nuts can be used. The modification described in the preceeding paragraph is, thus, increasing the versatility of the device. Using the device without connecting link gives on one side the advantage that the device becomes shorter and also lighter. Using the device without connecting link reduces on the other side the possibilities for adjusting the two holders and one loses also the possibility to exert a compressing or extending force on the bone by rotating the tensioning screw 69 in one direction or the other. Thus, the device will presumably usually be used with a connecting link and only in particular cases without connecting link.

One can also press a bush 193 into the open end portion of the hole 131$a$ extending over that portion of the body 131 that comprises the transverse through hole 131$b$ being farthest away from the extension 131$d$. This bush 193 comprises a through hole coaxial to the axis of the hole 131$a$ and forming a constriction at the open end of the hole 131$a$, a transverse hole corresponding to the through hole 131$b$ and also a tapped hole corresponding to that tapped hole 131$c$ that is farthest away from the extension 131$d$. One could then still mount a pin in the hole 131$b$ farthest away from the extension 131$d$. In place of that pin or possibly in addition to that pin one could also loosably fix a not shown supplemental elongate extension member formed by a tube or rod or the like inserted into the through hole of the bush. If the device serves for setting a bone of a leg of a person, the device can be mounted in such a way that the body 131 and the supplemental extension member look towards the foot of the patient and this extension member could comprise at its end remote from the body 131 a plate for supporting the foot of the patient.

It is also possible to attach additional positioning devices to the pins screwed into a bone if this is desirable.

What is claimed is:

1. A bone setting device comprising a plurality of pins for insertion into the bone fragments to be set, two elongated holders for retaining said pins, pin clamping means in said holders for clamping said pins, an elongated connecting link, each end of said link being hinged, with hinge means having a hinge bolt, to one of said holders and pivotable about an axis defined by the bolt and perpendicular to the longitudinal axes of the holders and the link, and holder clamping means for clamping said holders relative to said link at positions about said axes, at least one of said pin clamping means comprising a generally spherically shaped guiding body having at least one slot in its surface to provide compressibility in said body, a through hole in said body for receiving a pin and for enabling said pin to be pivoted in space, the holder in which the pin clamping means having the guiding body is positioned comprising two clamping elements each having at least one recess for receiving a portion of the guiding body and screw means for pressing said clamping elements together to compress and clamp the guiding body, said hinge means comprising tightening means enabling the holder to be locked to the link.

2. The device claimed in claim 1 wherein the screw means comprises two screws and the guiding body is positioned between the two screws.

3. The device claimed in claim 1 wherein the connecting link comprises a sleeve having a longitudinal hole and a stud positioned in said hole to slide along the axis of said hole, said stud itself comprising a longitudinal hole at least partly threaded and a tensioning screw having a head and a threaded portion engaging the threaded hole of said stud, said sleeve having at least one surface forming an angle with the axis of the tensioning screw for engaging the head of said tensioning screw whereby rotation of said tensioning screw moves said holders axially relative to one another, said connecting link being hinged to one of the holders through said sleeve and to the other holder through said stud.

4. The device claimed in claim 1 wherein the connecting link comprises at least one through hole for receiving a pin and means for clamping said pin in said through hole, said through hole maintaining said pin in a position such that its axis is substantially parallel to the axis of at least one of the hinges joining the connecting link with the holder.

5. The device claimed in claim 1 wherein said link comprises contact surfaces and each of said holders comprises a contact surface for engagement with a contact surface of said link, said surfaces having intermeshing serrations to lock said link against rotation relative to said holders, when said tightening means are tightened.

6. The device claimed in claim 1 wherein at least one of said holders comprises a generally cylindrical body having a longitudinal hole whose axis is parallel to but eccentric to the axis of the body; a plurality of transverse holes intersecting said longitudinal hole, for receiving pins, said transverse holes permitting longitudinal translation of the pins and rotation of the pins about their axes but restraining said pins from movement in other dimensions, and means for clamping the pins in the transverse holes.

7. The device claimed in claim 6 wherein the clamping means comprises threaded transverse holes perpendicular to the transverse holes for the pins, and screws in threaded holes.

8. The device as claimed in claim 1, wherein each of said hinge bolts has at least one threaded portion, a bearing portion and a head, enabling the holders to be locked to the links by tightening said hinge bolts.

9. The device claimed in claim 8 wherein the portions of the holder and the link hinged by one of said hinge bolts each has a hole for receiving a hinge bolt, at least one hole having an interior thread, each hinge bolt having a first threaded portion on the side of the bearing portion adjacent to the head and second threaded portion on the side of the bearing portion remote from the head, the first threaded portion being screwed into said interior thread in said one hole, the second threaded portion being thinner than the first to enable it to be pushed through said interior thread, the two threaded portions being threaded in opposite senses and a nut screwed onto the second threaded portion.

10. The device claimed in claim 1 wherein said at least one holder comprises at least two of said pin clamping means enabling said pins to be pivoted in space.

11. The device claimed in claim 1 wherein the two elongated holders and the connecting link are lockable by said tightening means in a position where their axes are aligned.

12. The device claimed in claim 3 wherein the head of said tensioning screw is accessible from outside the sleeve.

13. The device claimed in claim 3 wherein said surface of said sleeve is placed between said stud and said head so that said two holders can be pulled towards each other by rotating said tensioning screw in such a way that said head engages said surface.

14. The device claimed in claim 3 wherein the sleeve has an extension at one end eccentric with relation to the longitudinal axis of the sleeve, said extension and a portion of one of said holders being joined by one of said hinge bolts to said sleeve.

15. The device claimed in claim 14 wherein the longitudinal hole in said sleeve has an extension eccentric to the axis of the hole, and wherein said tensioning screw is also eccentric to the axis of said hole and passes through said hole extension into said stud, wherein said sleeve extension and said hole extension are generally on opposite sides of the axis of the sleeve.

16. The deivce claimed in claim 14 wherein said sleeve extension comprises a recess to accommodate the head of said tension screw and is limited on its side opposite said stud by a surface forming an angle with the axis of the tensioning screw so that said two holders can be pushed away from each other by rotating said tensioning screw in such a way that said head engages said surface limiting said recess.

17. The device claimed in claim 3, wherein said stud has at least one clamping surface, the device including a clamping screw and at least one threaded hole in said sleeve for receiving said clamping screw to enable said screw to contact a clamping surface to clamp said stud within said sleeve in different sliding positions.

18. The device in claim 17 wherein said clamping surface has in cross-section a form which is different from a circle around the axis of said stud so that said clamping surface and said clamping screw define together a position of rotation of said stud in relation to said sleeve.

19. The device claimed in claim 18 wherein said sleeve has at least two tapped holes transverse to the longitudinal hole of said sleeve spaced along the circumference of the sleeve for receiving said clamping screw.

20. The device claimed in claim 18 wherein said stud has at least two clamping surfaces spaced along the circumference of the stud for alternative engagement by the clamping screw.

21. The device as claimed in claim 17, said longitudinal hole of said sleeve having a circular cross-section so that said stud can be rotated in said sleeve and clamped at various positions of rotation.

22. The device claimed in claim 21 wherein at least one clamping surface comprises a plane parallel to the axis of the stud.

23. The device claimed in claim 21 wherein at least one clamping surface is within a groove.

24. A bone setting device comprising a plurality of pins for insertion into the bone fragments to be set, two elongated holders for retaining said pins, pin clamping means in said holders for clamping said pins, an elongated connecting link, each end of said link being hinged with hinge means having a hinge bolt to one of said holders and pivotable about an axis defined by the bolt and perpendicular to the longitudinal axes of the holders and the link, and means for clamping said holders relative to said link at positions about said axes, said connecting link comprising a sleeve having a longitudinal hole and a stud positioned in said hole and slidable along the axis of the hole, said stud itself comprising a second longitudinal hole at least partly threaded and a tensioning screw having a head and a threaded portion engaging the threaded hole of said stud, said sleeve having a surface forming an angle with the axis of the tensioning screw and an extension at the end forming said surface, said sleeve extension being eccentric with relation to the longitudinal axis of the sleeve and connected with a portion of one said holders by one of said hinge bolts, wherein the longitudinal hole in said sleeve has an extension eccentric to the axis of the hole, wherein said tensioning screw is also eccentric to the axis of said hole and passes through said hole extension into said stud, wherein said sleeve extension and said hole extension are generally on opposite sides of the axis of the sleeve, wherein the head of said tensioning screw is accessible from outside said sleeve, wherein said sleeve extension comprises a recess to accommodate the head of said tensioning screw and is limited on its side opposite said surface by another surface forming an angle with the axis of the tensioning screw, so that said two holders can be pulled towards or pushed away from each other by rotating said tensioning screw, thus bringing its head into engagement with said surface of said sleeve or said surface limiting said recess, and wherein said stud has at least one clamping surface within a longitudinal groove, said device including a clamping screw and at least one threaded hole in said sleeve for receiving said screw to enable said screw to protrude into said groove so that when the screw is loosened while still protruding into the groove, said stud can be axially displaced in a definite rotational position relative to the sleeve, and when the screw is tightened in firm contact with said clamping surface it can clamp said stud within said sleeve in one of different sliding positions.

25. The device claimed in claim 24 wherein at least one of said holders comprises two clamping elements each having a recess, each recess being opposed to the recess of the other element, and wherein said pin clamping means comprises a compressible, spherically shaped guiding body, having a through hole for receiving a pin, positioned in the recesses of said clamping elements and screw means for pressing said elements together, thereby compressing said guiding body to clamp a pin in said through hole.

26. The device claimed in claim 25 wherein the screw means comprises two screws.

27. The deivce claimed in claim 24 wherein the longitudinal hole of the sleeve has a circular cross-section so that the stud can be rotated in the sleeve and clamped at various positions of rotation.

28. The device claimed in claim 24 wherein the sleeve has at least two threaded holes transverse to the longitudinal hole of said sleeve spaced along the circumference of the sleeve for receiving the clamping screw.

29. The device claimed in claim 24 and comprising means for securing said elongated holders and said connecting link in a position where their axes are aligned.

30. The device claimed in claim 24 wherein each of said hinge bolts has a head, a first threaded portion adjacent said head, a second threaded portion, and a bearing portion between said first and second threaded portions and wherein each of the holders and the link have holes for receiving a hinge bolt, at least one of said holes having an interior thread, adapted to engage the first threaded portion of the hinge bolt, the second threaded portion of the hinge bolt being of reduced size to enable it to get through the interior thread without engagement therewith, the first and second threaded portions having different hands, and a nut engaging the second threaded portion.

* * * * *

UNITED STATES PATENT AND TRADEMARK OFFICE
CERTIFICATE OF CORRECTION

PATENT NO. : 4,714,076
DATED : December 22, 1987
INVENTOR(S) : Pierre-Andre Comte et al It is certified that error appears in the above—identified patent and that said Letters Patent is hereby corrected as shown below:

On the title page

Assignee: "Synthes, Paoli, Pa." should be

--Synthes (U.S.A.), Paoli, Pa.--

Signed and Sealed this

Fifth Day of July, 1988

Attest:

DONALD J. QUIGG

*Attesting Officer*  *Commissioner of Patents and Trademarks*